United States Patent [19]

McMenim

[11] 4,154,758

[45] May 15, 1979

[54] PROCESS FOR THE MANUFACTURE OF p-HYDROXYBENZYL CYANIDE

[75] Inventor: Michael E. McMenim, Macclesfield, England

[73] Assignee: Imperial Chemical Industries Limited, London, England

[21] Appl. No.: 908,464

[22] Filed: May 22, 1978

[51] Int. Cl.² ............... C07C 120/00; C07C 121/66
[52] U.S. Cl. .............................. 260/465 F; 260/559 R
[58] Field of Search ..................................... 260/465 F

[56] References Cited

U.S. PATENT DOCUMENTS 3,983,151 9/1976 Meyer ............................. 260/465 F
3,983,160 9/1976 Meyer ............................. 260/465 F

OTHER PUBLICATIONS

C.A., 82, (1975), Hayashi et al., 124965f.
C.A., 85, (1976), Schwartz et al., 46160k.
C.A., 85, (1976), Meyer, 46229q.

Primary Examiner—Joseph Paul Brust
Attorney, Agent, or Firm—Cushman, Darby & Cushman

[57] ABSTRACT

A process for the manufacture of p-hydroxybenzyl cyanide which comprises reacting p-hydroxyphenylglycine acid with cyanide ion. The product is a useful intermediate for the preparation of the β-adrenergic blocking agent atenolol.

9 Claims, No Drawings

PROCESS FOR THE MANUFACTURE OF p-HYDROXYBENZYL CYANIDE

This invention relates to a new chemical process for the manufacture of the compound p-hydroxybenzyl cyanide, which is a valuable chemical intermediate.

According to the invention there is provided a process for the manufacture of p-hydroxybenzyl cyanide which comprises reacting α-(p-hydroxyphenyl)glycine [α-amino-α-(p-hydroxyphenyl)acetic acid] with cyanide ion.

The cyanide ion is conveniently provided in the form of an alkali metal cyanide, for example sodium or potassium cyanide.

The reaction is conveniently carried out in a relatively high-boiling, dipolar, aprotic solvent, for example N,N-dimethylformamide, 2-pyrrolidone, N-methyl-2-pyrrolidone or dimethyl sulphoxide. Other relatively high-boiling polar solvents, for example n-butanol, 3-methylbutanol, acetamide or 2-ethoxyethanol are also satisfactory solvents and some such solvents, for example water, ethylene glycol, formamide and urea, are suitable although less satisfactory.

The reaction is conveniently carried out at a temperature of between 100° and 250° C., preferably at a temperature of between 120° and 190° C.

The reaction may optionally be carried out in the presence of a base, for example an alkali metal hydroxide, for example sodium or potassium hydroxide.

The α-(p-hydroxyphenol)glycine used as starting material is a known compound.

As stated above, p-hydroxybenzyl cyanide is a valuable chemical intermediate, and in particular it is a valuable intermediate for use, by hydrolysis, in the preparation of p-hydroxyphenylacetamide, which in turn is a valuable intermediate for the preparation of the β-adrenergic blocking agent p-(2-hydroxy-3-isopropylaminopropoxy)phenylacetamide.

The invention is illustrated but not limited by the following Examples:

EXAMPLE 1

Sodium cyanide (3.0 g.) is added to a stirred solution of p-hydroxyphenylglycine (10.0 g.) and sodium hydroxide (2.4 g.) in N,N-dimethylformamide (20 ml.) at 80° C., and the mixture is then stirred and heated at 130° C. for 1 hour and cooled to 20° C. Water (25 ml.) is added and the mixture is acidified to pH 5 with concentrated aqueous hydrochloric acid and extracted four times with diethyl ether (40 ml. each time). The combined extracts are dried and evaporated to dryness and the residue is distilled at a pressure of 0.05 mm. Hg. There is thus obtained as distillate, which solidifies on cooling, p-hydroxybenzyl cyanide, m.p. 68°–69° C. (6.37 g.; 80% yield).

EXAMPLE 2

The process described in Example 1 is repeated except that isobutyl methyl ketone is used in place of diethyl ether to extract the reaction mixture. The combined extracts are dried but not evaporated to dryness, and there is thus obtained a solution containing p-hydroxybenzyl cyanide which is suitable for hydrolysis to p-hydroxyphenylacetamide without further isolation or purification.

What we claim is:

1. A process for the manufacture of p-hydroxybenzyl cyanide which comprises reacting α-(p-hydroxyphenyl)glycine with an alkali metal cyanide in a solvent at a temperature of between 100° C. and 250° C.

2. A process as claimed in claim 1 wherein the alkali metal cyanide is sodium or potassium cyanide.

3. A process as claimed in claim 2 which is carried out in a dipolar, aprotic solvent.

4. A process as claimed in claim 3 wherein the solvent is N,N-dimethylformamide, 2-pyrrolidone, N-methyl-2-pyrrolidone or dimethyl sulphoxide.

5. A process as claimed in claim 1, which is carried out in n-butanol, 3-methylbutanol, acetamide or 2-ethoxyethanol as solvent.

6. A process as claimed in claim 1, which is carried out in water, ethylene glycol, formamide or urea as solvent.

7. A process as claimed in claim 1 which is carried out at a temperature of between 120° and 190° C.

8. A process as claimed in claim 1 which is carried out in the presence of alkali metal hydroxide.

9. A process as claimed in claim 8 wherein the base is sodium or potassium hydroxide.